United States Patent
Kopperschmidt

(10) Patent No.: US 8,574,183 B2
(45) Date of Patent: Nov. 5, 2013

(54) METHOD AND DEVICE FOR MONITORING A BLOOD TREATMENT UNIT OF AN EXTRACORPOREAL BLOOD TREATMENT DEVICE

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 718 days.

(21) Appl. No.: 12/598,250

(22) PCT Filed: Apr. 29, 2008

(86) PCT No.: PCT/EP2008/003439
§ 371 (c)(1),
(2), (4) Date: Nov. 25, 2009

(87) PCT Pub. No.: WO2008/135193
PCT Pub. Date: Nov. 13, 2008

(65) Prior Publication Data
US 2010/0137777 A1    Jun. 3, 2010

(30) Foreign Application Priority Data
May 4, 2007   (DE) .......................... 10 2007 020 934

(51) Int. Cl.
*A61M 37/00* (2006.01)
(52) U.S. Cl.
USPC ........................... 604/5.04; 210/645; 210/646
(58) Field of Classification Search
USPC ....................................................... 604/5.04
See application file for complete search history.

(56) References Cited

U.S. PATENT DOCUMENTS 4,444,596 A  *  4/1984  Gortz et al. ..................... 134/18
5,429,486 A  *  7/1995  Schock et al. ................ 417/476
(Continued)

FOREIGN PATENT DOCUMENTS

DE   19734002 C1   9/1998
DE   19901078 C1   2/2000
(Continued)

OTHER PUBLICATIONS

International Search Report, PCT/EP2008/003439, mailed Aug. 21, 2008.
(Continued)

Primary Examiner — Tatyana Zalukaeva
Assistant Examiner — Ginger T Chapman
(74) Attorney, Agent, or Firm — Kenyon & Kenyon LLP

(57) ABSTRACT

The present invention relates to a method and a device for monitoring a blood treatment unit, subdivided by a semipermeable membrane into a blood chamber and a dialysis liquid chamber, of an extra-corporeal blood treatment device, which comprises an extra-corporeal blood circuit having an arterial branch leading to the blood chamber of the blood treatment unit, a venous branch, which extends away from the blood chamber, and a dialysis fluid system, in which the dialysis liquid chamber is arranged. The method according to the present invention and the device according to the present invention are based on the idea that the change of the flow resistance of the dialysis machine is determined based on two measurements, wherein an oscillating pressure signal in the extra-corporeal blood circuit or in the dialysis fluid system is measured before and after the change of the substitution rate and/or ultrafiltration rate, with which the substitute is applied to, or ultrafiltrate is removed from, the blood flowing in the blood circulation system. Preferably, the supply of substitute is interrupted temporarily.

11 Claims, 3 Drawing Sheets

(56) References Cited

U.S. PATENT DOCUMENTS

| | | | |
|---|---|---|---|
| 6,077,443 | A | 6/2000 | Goldau |
| 6,623,443 | B1 | 9/2003 | Polaschegg |
| 6,745,630 | B2 | 6/2004 | Gross |
| 8,460,552 | B2 * | 6/2013 | Kopperschmidt et al. .... 210/645 |
| 2002/0174721 | A1 | 11/2002 | Gross |
| 2005/0065459 | A1 | 3/2005 | Zhang et al. |
| 2006/0157408 | A1 | 7/2006 | Kuroda et al. |
| 2006/0254982 | A1 | 11/2006 | Kopperschmidt |
| 2007/0108128 | A1 | 5/2007 | Kopperschmidt et al. |

FOREIGN PATENT DOCUMENTS

| | | |
|---|---|---|
| DE | 10115991 C1 | 4/2002 |
| DE | 10355042 B3 | 6/2005 |
| DE | 102004023080 | 12/2005 |
| EP | 328162 A2 * | 8/1989 |
| EP | 0330761 A | 9/1989 |
| EP | 1595560 A | 9/2009 |
| JP | 07-080060 | 3/1995 |
| JP | 2004-248844 | 9/2004 |
| JP | 2005-511151 | 4/2005 |
| JP | 2005-233681 | 9/2005 |
| JP | 2005-324024 | 11/2005 |
| WO | WO 00/12991 A1 * | 3/2000 |
| WO | 03/047656 A | 6/2003 |
| WO | 2004/073772 | 9/2004 |
| WO | 2005/058390 A1 | 6/2005 |
| WO | WO 2007/012915 A1 * | 2/2007 |

OTHER PUBLICATIONS

International Preliminary Report on Patentability for PCT/EP2008/003439, mailed on Dec. 7, 2009.

* cited by examiner

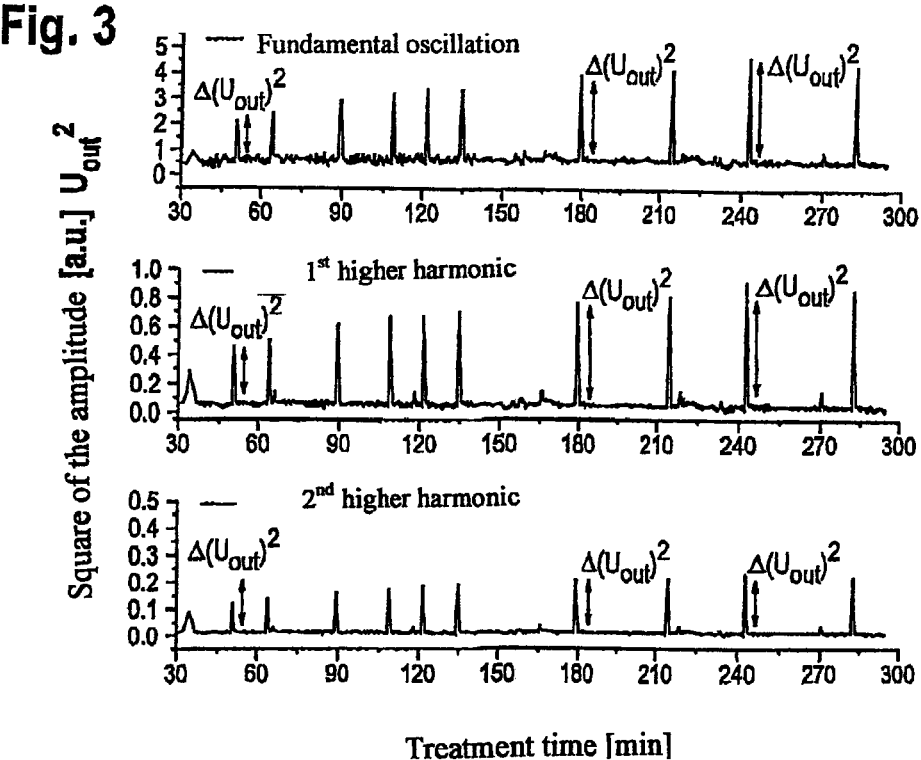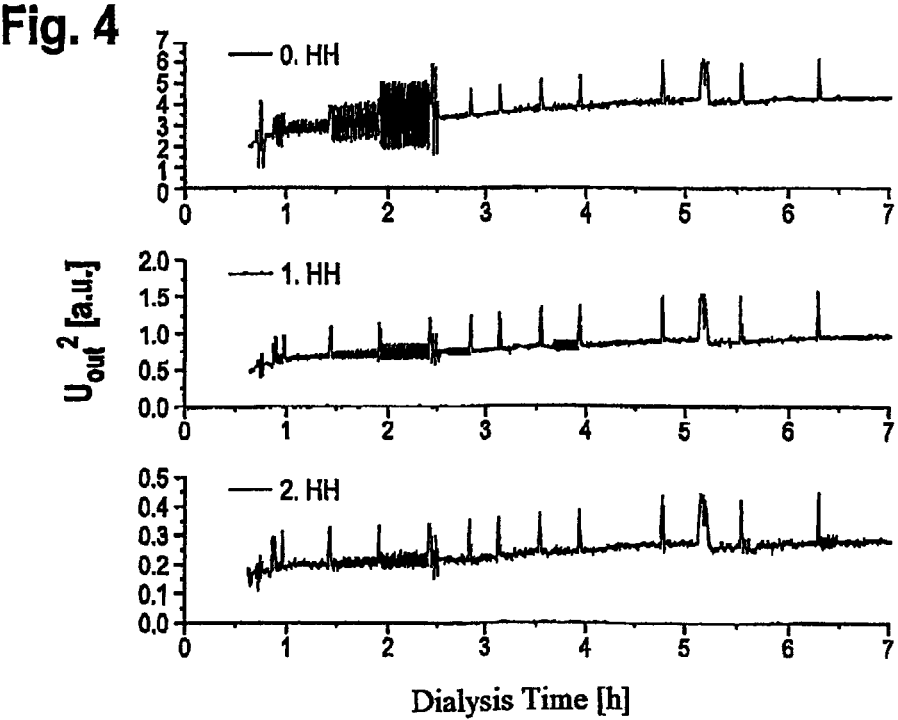

| HDF Postdilution (diagram 1-3) | $\Delta U_{out}^2$ | $U_{out}^2$ | $(R+\Delta R)/R$ |
|---|---|---|---|
| *Towards start of treatment* | | | |
| Fundamental oscillation | 1.47 | 2.08 | 1.85 |
| 1st higher harmonic | 0.38 | 0.45 | 2.54 |
| 2nd higher harmonic | 0.11 | 0.13 | 2.55 |
| *Middle of treatment* | | | |
| Fundamental oscillation | 3.38 | 3.97 | 2.59 |
| 1st higher harmonic | 0.71 | 0.76 | 3.90 |
| 2nd higher harmonic | 0.2 | 0.21 | 4.58 |
| *Towards end of treatment* | | | |
| Fundamental oscillation | 4.01 | 4.69 | 2.63 |
| 1st higher harmonic | 0.81 | 0.87 | 3.81 |
| 2nd higher harmonic | 0.22 | 0.23 | 4.80 |

Table 1

Fig. 5

| HDF Predilution (diagram 4-6) | $\Delta U_{out}^2$ | $U_{out}^2$ | $(R+\Delta R)/R$ |
|---|---|---|---|
| *Towards start of treatment* | | | |
| Fundamental oscillation | 0.88 | 3.86 | 1.14 |
| 1st higher harmonic | 0.33 | 0.99 | 1.22 |
| 2nd higher harmonic | 0.1 | 0.3 | 1.22 |
| *Middle of treatment* | | | |
| Fundamental oscillation | 1.46 | 5.275 | 1.18 |
| 1st higher harmonic | 0.52 | 1.36 | 1.27 |
| 2nd higher harmonic | 0.124 | 0.38 | 1.22 |
| *Towards end of treatment* | | | |
| Fundamental oscillation | 1.89 | 6.19 | 1.20 |
| 1st higher harmonic | 0.72 | 1.7 | 1.31 |
| 2nd higher harmonic | 0.17 | 0.44 | 1.28 |

Fig. 6

METHOD AND DEVICE FOR MONITORING A BLOOD TREATMENT UNIT OF AN EXTRACORPOREAL BLOOD TREATMENT DEVICE

CROSS REFERENCE TO RELATED APPLICATIONS

This is a 371 national phase application of PCT/EP2008/003439 filed Apr. 29, 2008, claiming priority to German Patent Application No. 10 2007 020 934.9 filed May 4, 2007.

FIELD OF INVENTION

The present invention relates to a method for monitoring a blood treatment unit of an extracorporeal blood treatment apparatus, said blood treatment unit being divided by a semipermeable membrane into a blood chamber and a dialyzing fluid chamber, the blood treatment apparatus comprising an extracorporeal blood circuit with an arterial branch that leads to the blood chamber of the blood treatment unit, and a venous branch that leads away from the blood chamber, and a dialyzing fluid system in which the dialyzing fluid chamber is disposed. Moreover, the present invention relates to a device for monitoring a blood treatment unit for an extracorporeal blood treatment apparatus, said blood treatment unit being divided by a semipermeable membrane into a blood chamber and a dialyzing fluid chamber, as well as an extracorporeal blood treatment apparatus with a device for monitoring the blood treatment unit.

BACKGROUND OF THE INVENTION

For the purpose of removing substances usually eliminated with urine and for the purpose of withdrawing fluid, use is made of various methods for machine-aided blood treatment in acute or chronic kidney failure. In the case of hemodialysis (HD), a patient's blood is conveyed in an extracorporeal blood circuit through one chamber of a dialyzer divided by a semipermeable membrane into two chambers, whilst a dialyzing fluid flows through the other chamber. A diffusive substance exchange essentially takes place via the membrane of the dialyzer. Only a convective substance exchange is present in the case of hemofiltration (HF). Hemodiafiltration (HDF) is a combination of the two methods.

The fluid withdrawn via the membrane of the dialyzer from the blood flowing in the extracorporeal blood circuit is referred to as ultrafiltrate. In the case of hemodiafiltration, a part of the ultrafiltrate withdrawn through the membrane of the dialyzer is replaced by a sterile substitution fluid, which is fed back to the extracorporeal blood circuit either upstream of the dialyzer (pre-dilution) or downstream of the dialyzer (post-dilution). Pre- and post-dilution can also take place at the same time. The sterile substituate, which is fed to the blood circuit, can be prepared online from the dialyzing fluid. The quantity of substituate that is fed in a specific period to the blood flowing in the extracorporeal blood circuit is referred to as the substituate rate. The rate at which fluid is withdrawn from the patient is referred to as the net withdrawal rate, as well as the ultrafiltration rate in general linguistic usage. The latter emerges as the difference between the substitution rate and the rate of the fluid displacement across the membrane.

It has been shown that an HDF blood treatment in which a post-dilution takes place has a higher efficiency, with an identical substituate rate, than a treatment in which a pre-dilution takes place. The higher cleaning capacity with the post-dilutive addition of substitution fluid compared to the pre-dilutive addition of substitution fluid is due to the fact that the filtrate is obtained completely from the blood to be cleaned in the case of post-dilution, whereas in the case of pre-dilution the blood diluted with substituate flows into the dialyzer (DE 103 55 042 B3).

The flow resistance of the membrane of the dialyzer is of importance for an extracorporeal blood treatment. With an excessively high flow resistance, the blood to be cleaned in the extracorporeal blood circuit may possibly not be able to be conveyed at the required delivery rate, as a result of which the effectiveness of the blood treatment is reduced. A greatly increased flow resistance of the dialyzer can even lead to complete blocking-up of the membrane. The treatment is then interrupted and, the whole blood hose system may have to be replaced (DE 103 55 042 B3). The effectiveness of the blood treatment itself, with an unchanged delivery rate, is reduced by the influence of the exchange surfaces of the membrane, in particular also the pores of the membrane itself.

DE 103 55 042 B3 describes a method for detecting disruptions of the blood flow in an extracorporeal blood circuit during an extracorporeal blood treatment with an extracorporeal blood treatment apparatus. The known method is based on the analysis of an oscillating pressure signal propagated in the extracorporeal blood circuit which is measured and analyzed, the phase angle of at least one harmonic of the pressure signal being determined. A disruption of the blood flow in the extracorporeal blood circuit is detected on the basis of the change in the phase angle of the at least one harmonic.

A method of detecting the clogging of the membrane of a dialyzer is known from WO 2004/073772 A1. The known method is based on an analysis of the frequency spectrum of a pressure signal transmitted via the dialyzer. During the blood treatment, the pressure conditions in the extracorporeal blood circuit and/or in the dialyzing fluid system are continuously monitored. While the pressure in the extracorporeal circuit and/or the dialyzing substituate rate and the ultrafiltration rate remain unchanged.

US 2002/0174721 A1 and U.S. Pat. No. 6,623,443 BI describe methods for detecting stenoses in a hose line system of an extracorporeal blood circuit. The two methods are based on an analysis of pressure pulses which are detected in the extracorporeal blood circuit. The method known from US 2002/0174721 A1 makes provision for analyzing the frequency spectrum of the pressure pulses and determining the attenuation of at least one harmonic of the pressure signal, it being concluded that there is a stenosis if there is a change in the attenuation. A change in the substituate or ultrafiltration rate is not taken into account in the analysis of the pressure pulses.

SUMMARY OF THE INVENTION

One problem underlying the present invention is to provide a method for monitoring a blood treatment unit divided by a semipermeable membrane into a blood chamber and a dialyzing fluid chamber, which method permits the determination of a quantity providing information for maintaining the blood flow in the extracorporeal blood circuit or the cleaning performance of the blood treatment unit.

Moreover, a problem underlying the present invention is to provide a device for monitoring a blood treatment unit of an extracorporeal blood treatment apparatus, which device enables a determination of a quantity providing information for maintaining the blood flow in the extracorporeal blood circuit or the cleaning performance of the blood treatment unit. A further problem underlying the present invention is to make available a blood treatment apparatus with a device for monitoring the blood treatment unit.

The method according to the present invention and the device according to the present invention require that substituate can be fed upstream or downstream of the blood treatment unit to the blood in the extracorporeal blood circuit at a preset substituate rate, which can be greater than or equal to zero (no substituate is fed), and/or that ultrafiltrate can be withdrawn via the semipermeable membrane of the blood treatment unit at a preset ultrafiltration rate, which again can be greater than or equal to zero (no ultrafiltrate is withdrawn).

The method according to the present invention and the device according to the present invention are essentially based on the fact that different conditions are created in the dialyzer or filter, and a measurement takes place in each case. This can take place in particular by changing the viscosity of the blood upstream of the dialyzer or filter (pre-dilution) and/or by changing the viscosity of the blood in the dialyzer or filter. The change in the viscosity of the blood can be brought about by the fact that substituate is fed to the blood in the extracorporeal circuit and/or ultrafiltrate is removed via the semipermeable membrane of the dialyzer or filter. A change in the substituate rate and/or the ultrafiltration rate thus leads to a change in the viscosity of the blood.

The monitoring of the blood treatment unit of the extracorporeal blood treatment apparatus is based on two measurements at different times. The first measurement takes place at a time when substituate is fed at a preset first substituate rate or no substituate is fed upstream or downstream of the blood treatment unit to the extracorporeal blood circuit, and/or ultrafiltrate is withdrawn at a preset first ultrafiltration rate or no ultrafiltrate is withdrawn via the semipermeable membrane of the blood treatment unit, and the second measurement takes place when substituate is fed at a preset second substituate rate or no substituate is fed to the extracorporeal blood circuit, the second substituate rate differing from the first substituate rate, and/or ultrafiltrate is withdrawn at a preset second ultrafiltration rate or no ultrafiltrate is withdrawn via the membrane of the blood treatment unit, the second ultrafiltration rate differing from the first ultrafiltration rate. The substituate rate and the ultrafiltrate rate can be greater than or equal to zero.

It is unimportant whether the first or the second measurement is carried out first. The only decisive factor is that different substituate rates and/or ultrafiltration rates are set in the two measurements. For example, the substituate rate can be raised or lowered by a preset value. The simplest case is that in which, in the first measurement, the blood treatment apparatus is operated at a preset substituate rate and/or ultrafiltration rate which is greater than zero, the substitution of substituate or the withdrawal of ultrafiltrate being interrupted for the second measurement. Alternatively, it is also possible to interrupt the substitution and/or ultrafiltration in the first measurement and to operate the blood treatment apparatus at a preset substituate rate and/or ultrafiltration rate in the second measurement.

On the basis of the measured oscillating pressure signals before and after the change in the substituate rate and/or the ultrafiltration rate, a quantity correlating with the change in the flow resistance of the blood treatment unit is calculated.

In a preferred embodiment, when the substituate rate for the first and second measurement is changed, a change in the ultrafiltration rate at which a preset quantity of ultrafiltrate is withdrawn from the extracorporeal blood circuit is also carried out. In this connection, ultrafiltration rate is understood below to mean not the "net withdrawal rate", but the rate at which fluid is displaced across the membrane of the dialyzer or filter.

At the time at which substituate is fed at the preset first substituate rate, a first ultrafiltration rate is set, whilst at the time at which substituate is fed at the second substituate rate, a second ultrafiltration rate is set. The ultrafiltration rate is preferably increased or reduced by the same amount as the substituate rate is increased or reduced. The increase or reduction in the substituate rate and the ultrafiltration rate should preferably take place simultaneously. This is not however absolutely essential. A certain period can therefore lie between the change in the substituate rate and the ultrafiltration rate.

The quantity correlating with the change in the flow resistance can be compared with a preset threshold value, it being concluded that there is a critical state if the quantity correlating with the change in the flow resistance exceeds the preset threshold value.

In the case where it is concluded that there is a critical state, an intervention can be made in the blood treatment in order to counteract the critical state. The substituate rate or the ultrafiltration rate can for example be changed. In any event, the membrane of the blood treatment unit should be prevented from clogging up.

It is also possible to monitor the quantity correlating with the change in the flow resistance in that it is compared with the preset threshold value, an acoustic and/or optical alarm being emitted after it is exceeded.

A preferred embodiment makes provision such that the calculation of the quantity correlating with the change in the flow resistance is based on an analysis of the frequency spectrum of the oscillating pressure signal measured before the change in the substituate rate and the oscillating pressure signal measured after the change in the substituate rate, the change in the amplitude of the fundamental oscillation and/or the change in the amplitude of at least one harmonic of the oscillating pressure signal measured before and after the change in the substituate rate being determined. The change in the flow resistance can then be calculated on the basis of the change in the amplitude of the fundamental oscillation and/or the at least one harmonic. In practice, it may be sufficient for the amplitude change in the fundamental oscillation alone to be evaluated.

The analysis of the measured pressure signals preferably takes place with a Fourier transform. Other methods are however also possible which are known to the person skilled in the art, for example the least-square method, with which an attempt is made to reproduce the measured values through an adapted linear combination of basic functions.

For the method according to the present invention and the device according to the present invention, it is in principle irrelevant how the oscillating pressure signals are generated in the extracorporeal blood circuit. It is advantageous if the oscillating pressure pulses are evaluated that are generated by the blood pump, in particular an occluding blood pump, disposed in the extracorporeal blood circuit.

For the determination of the quantity correlating with the change in the flow resistance, it is also possible in principle to measure the oscillating pressure signals in the extracorporeal blood circuit or in the dialyzing fluid system, since a change in the flow resistance generally involves both a longitudinal and a lateral component.

With the known blood treatment apparatuses, the occluding blood pump, in particular a roller pump, generating an oscillating pressure signal is generally arranged in the arterial branch of the extracorporeal blood circuit. The oscillating pressure pulses of the blood pump, which run through the blood chamber of the blood treatment unit in the extracorporeal blood circuit, can be measured as an oscillating pressure signal in the venous branch of the extracorporeal circuit. This pressure signal is representative of the change in the flow resistance along the fibers of the dialyzer. The pressure pulses, which are transmitted via the membrane of the blood treatment unit and are characteristic of the flow resistance at right angles to the fibers of the dialyzer, can be measured as oscillating pressure signals in the dialyzing fluid system. The pressure pulses are preferably detected downstream of the blood treatment unit in the dialyzing fluid discharge line. In principle, however, the pressure pulses can also be measured in the dialyzing fluid supply line.

The device according to the present invention for monitoring the blood treatment unit can be a separate device or a component of the extracorporeal blood treatment apparatus. Since individual components of the monitoring device according to the present invention are already contained in the known blood treatment apparatuses, integration into the blood treatment apparatus is suitable. For example, the known dialysis apparatuses generally have pressure sensors in the extracorporeal blood circuit and in the dialyzing fluid system. In this regard, the monitoring device according to the present invention can be implemented in the known dialysis apparatuses without major expenditure on hardware.

BRIEF DESCRIPTION OF THE DRAWINGS

An example of embodiment of the present invention is explained in the greater detail below by reference to the drawings.

In the figures:

FIG. 3 shows the square of the amplitude of the fundamental oscillation as well as the first and second harmonic of the measured oscillating pressure signal as a function of the treatment time in the case of hemodiafiltration with post-dilution.

FIG. 4 shows the square of the amplitude of the fundamental oscillation as well as the first and second harmonic of the oscillating pressure signal as a function of the treatment time in the case of hemodiafiltration with pre-dilution.

FIG. 5 shows a table from which the change in the flow resistance of the blood treatment unit in the case of hemodiafiltration (HDF) with post-dilution during the blood treatment can be seen.

FIG. 6 shows a table from which the change in the flow resistance in the case of hemodiafiltration (HDF) with pre-dilution during the blood treatment can be seen.

DETAILED DESCRIPTION OF THE DRAWINGS

The theoretical principles of the method according to the present invention are described below by reference to a dialyzer divided by a semipermeable membrane into a dialyzing fluid chamber and a blood chamber, the blood chamber of the dialyzer being arranged in an extracorporeal blood circuit and the dialyzing fluid chamber in a dialyzing fluid system.

The longitudinal flow resistance in the dialyzer, i.e. the flow resistance along the fibers of the membrane of the dialyzer on the blood side, depends primarily on the flow rate of the blood through the fibers of the dialyzer, the viscosity of the blood flowing through the blood chamber of the dialyzer, which is equivalent to the local hematocrit in the dialyzer, as well as the cross-section and the length of the fibers.

With hemodiafiltration treatment (HDF), blood serum is transferred by means of increased convective transport via the dialyzer membrane onto the dialyzing fluid side, whilst substituate is substituted pre-dilutively, i.e. upstream of the dialyzer, or postdilutively, downstream of the dialyzer, in order to maintain the volume balance. The flow resistance of the blood to be dialyzed along the dialyzer fibers is strongly influenced by the convective withdrawal. A high flow resistance in the dialyzer can lead to a filter inlet pressure exceeding the occlusion pressure of the blood pump, so that there is the risk of mechanical hemolysis, or to a complete blocking-up of the fibers in the dialyzer, which is also referred to as clotting of the dialyzer. The thickening of the blood to be dialyzed due to a high convective water removal also leads to an increased flow resistance lateral to the dialyzer fibers. The convective withdrawal quantity, which corresponds to the substituate rate, should ideally be selected such that as large a convective transport as possible is enabled with a still stable, non-divergent flow resistance in the dialyzer.

The present invention proposes a measured quantity which corresponds to the change in the dynamic longitudinal or lateral flow resistance of the dialyzer of a hemodiafiltration treatment compared to a hemodialysis treatment.

Figure 1:
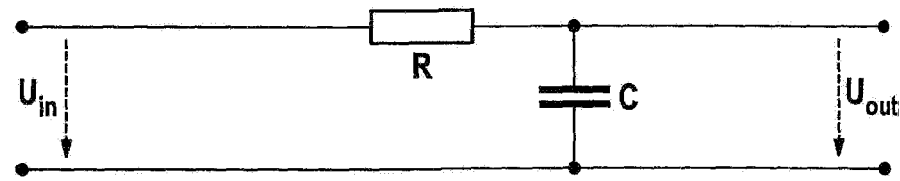
FIG. 1 shows a simplified electrical equivalent circuit diagram for representing the flow conditions in a blood treatment unit of an extracorporeal blood treatment apparatus.

The flow conditions in the dialyzer can be described with the simplified electrical circuit diagram from FIG. 1. According to the simplified representation of the flow conditions in the dialyzer by means of the electrical analogy, the dialyzer functions as a low pass for the pressure pulses ($U_{in}$) generated by the blood pump. This low pass is defined by the product RC. The resistance denoted by R in the analogy is equivalent to the longitudinal flow resistance of the dialyzer.

Oscillating input signal $U_{in}$ leads to a frequency-dependent attenuated output signal $U_{out}$. The relationship between $U_{in}$ and $U_{out}$ with $\omega$ as the periodicity of input signal $U_{in}$ reads as follows:

$$U_{out}(\omega t) = \frac{U_{in}(\omega t)}{1 + i\omega RC}, \quad (1)$$

where i denotes the complex unit.

An input signal $U_{in}$ oscillating with frequency $\omega$ leads according to equation (1) to an amplitude attention of output signal $U_{out}$:

$$U_{in}(\omega t) = (A + iB) \cdot e^{i\omega t} \quad (2)$$
$$U_{in}^*(\omega t) = (A - iB) \cdot e^{-i\omega t}$$
$$U_{out}^2 = U_{out}(\omega t) \cdot U_{out}^*(\omega t)$$
$$= \frac{(A + iB) \cdot e^{i\omega t}}{1 + i\omega RC} \cdot \frac{(A + iB) \cdot e^{-i\omega t}}{1 - i\omega RC}$$
$$= \frac{A^2 + B^2}{1 + \omega^2 R^2 C^2},$$

where the complex conjugated representation of U is denoted by U*.

The interesting quantity of the longitudinal dialyzer flow resistance or the longitudinal dialyzer impedance reads as $R(\omega)$. Elementary conversions yield the relationship:

$$R(\omega) = \frac{1}{\omega C}\sqrt{\left(\frac{U_{in}^2(\omega)}{U_{out}^2(\omega)} - 1\right)}, \quad (3)$$

where $U_{in}^2$ denotes the absolute square of the amplitude of input signal $U_{in}$ and $U_{out}^2$ denotes the absolute square of the amplitude of output signal $U_{out}$.

If the square of the amplitude of received signals $U_{out}^2$ changes by $\Delta U_{out}^2$, resistance R changes by $\Delta R$ according to equation (3).

$$\frac{R+\Delta R}{R} = \sqrt{\frac{\left(\frac{U_{in}^2(\omega)}{U_{out}^2(\omega)-\Delta U_{out}^2(\omega)}-1\right)}{\left(\frac{U_{in}^2(\omega)}{U_{out}^2(\omega)}-1\right)}} = \quad (4)$$

$$= \sqrt{\frac{U_{in}^2(\omega)-U_{out}^2(\omega)+\Delta U_{out}^2(\omega)}{U_{out}^2(\omega)-\Delta U_{out}^2(\omega)} \cdot \frac{U_{out}^2(\omega)}{U_{in}^2(\omega)-U_{out}^2(\omega)}} =$$

$$= \sqrt{\frac{U_{out}^2(\omega)}{U_{out}^2(\omega)-\Delta U_{out}^2(\omega)}\left(1+\frac{\Delta U_{out}^2(\omega)}{U_{in}^2(\omega)-U_{out}^2(\omega)}\right)}$$

The change in the flow resistance $(\Delta R+R)/R$ accordingly depends on the square of the amplitude of input signal $U_{in}$, which however is generally not known. On the plausible assumption that the attenuation of the pressure signal is great, the following holds approximately:

$$\frac{\Delta U_{out}^2(\omega)}{U_{in}^2(\omega)-U_{out}^2(\omega)} \ll 1, \quad (5)$$

so that there follows according to equation (4):

$$\frac{R+\Delta R}{R} \approx \sqrt{\frac{U_{out}^2(\omega)}{U_{out}^2(\omega)-\Delta U_{out}^2(\omega)}}. \quad (6)$$

From the ascertained signal intensities and their change, therefore, it is possible to draw conclusions about the change in the relative flow impedance along the dialyzer fibers with a specific frequency of the excitation, i.e. the multiple of the speed of the blood pump. The changed signal intensities upon transition from the blood side to the dialyzing fluid side are ascertained in order to calculate the flow impedance lateral to the dialyzer fibers.

If the condition assumed above (equation 5) is not met, $U_{out}^2(\omega)$ must be determined. The square of the amplitude of the input signal can be determined by measuring the oscillating pressure signal of the blood pump in the extracorporeal blood circuit upstream of the dialyzer and calculating the real part of the spectral component of the pressure signal. As an alternative, however, it is also possible to determine the RC component of the electrical power consumption of the blood pump.

It is not in principle necessary to determine the quantity "R" in order to perform the teaching according to the present invention. In principle, the quantity "U" or "$U^2$" can be evaluated in order to monitor the blood treatment unit.

Figure 2:
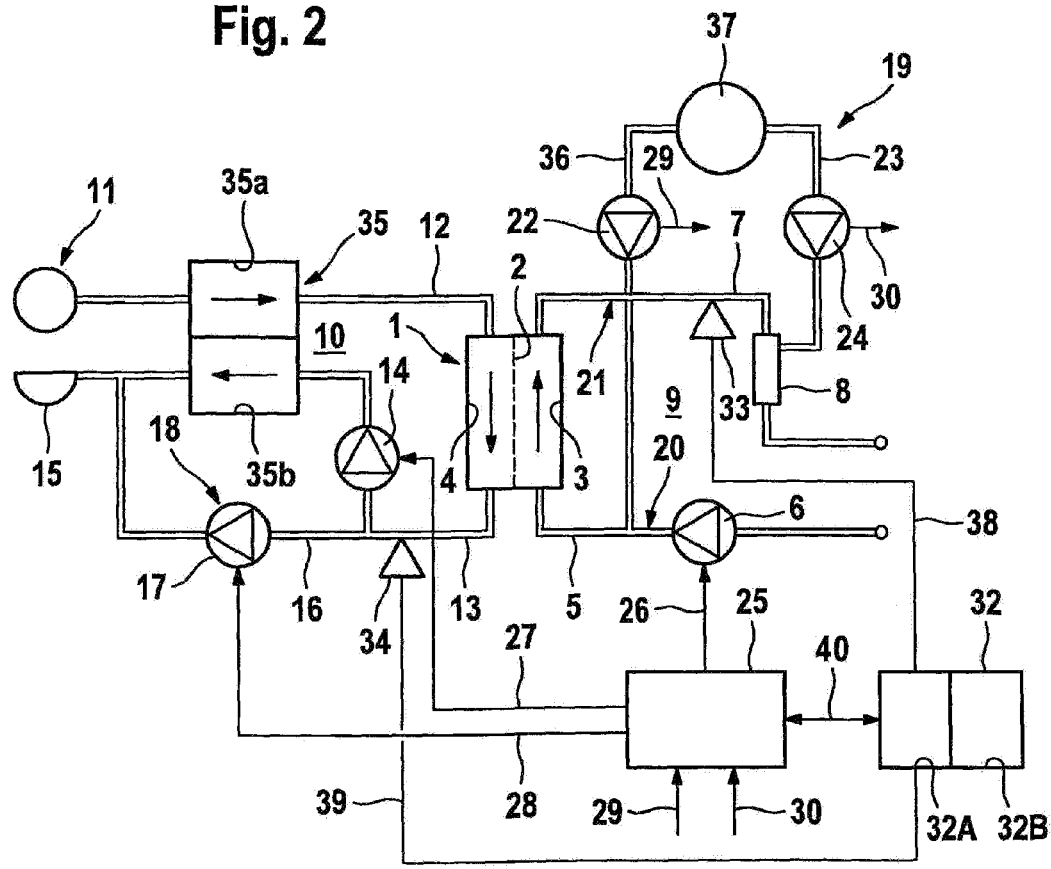
FIG. 2 shows the main components of an extracorporeal blood treatment apparatus according to the present invention together with a device according to the present invention for monitoring the blood treatment unit of the blood treatment apparatus in a simplified schematic representation.

FIG. 2 shows the main components of the blood treatment apparatus according to the present invention together with the monitoring device according to the present invention. The blood treatment apparatus is a hemodiafiltration apparatus which comprises a dialyzer or filter 1 as a blood treatment unit, said dialyzer or filter being divided by a semipermeable membrane 2 into a blood chamber 3 and a dialyzing fluid chamber 4. The inlet of blood chamber 3 is connected to one end of a blood supply line 5, in which a blood pump 6, in particular a roller pump generating a pressure pulse, is incorporated, whilst the outlet of the blood chamber is connected to one end of a blood discharge line 7, in which a drip chamber 8 is incorporated. Blood supply line and blood discharge line 5, 7 form, with blood chamber 3 of the dialyzer, extracorporeal blood circuit 9 of the hemodiafiltration apparatus. Blood supply line and blood discharge line 5, 7 are tube lines of a tube set (disposable) installed in the hemodiafiltration apparatus.

Dialyzing fluid system 10 of the hemodiafiltration apparatus comprises a device 11 for making available dialyzing fluid, which device is connected via the first section of a dialyzing fluid supply line 12 to the inlet of first chamber half 35a of a balancing device 35. The second section of dialyzing fluid supply line 12 connects the outlet of first balancing chamber half 35a to the inlet of dialyzing fluid chamber 4. The outlet of dialyzing fluid chamber 4 is connected via the first section of a dialyzing fluid discharge line 13 to the inlet of second balancing chamber half 35b. A dialyzing fluid pump 14 is incorporated in the first section of dialyzing fluid discharge line 13. The outlet of second balancing chamber half 35b is connected via the second section of dialyzing fluid discharge line 13 to a drain 15. Branching off from dialyzing fluid discharge line 13 upstream of dialyzing fluid pump 14 is an ultrafiltrate line 16, which also leads to drain 15. An ultrafiltration pump 17 is incorporated in ultrafiltrate line 16. Balancing device 35 consists of commercially available devices comprising two parallel balancing chambers which are operated anti-cyclically. For reasons of simplicity, however, there is no need to go into this further at this point.

During the dialysis treatment, the patient's blood flows through blood chamber 3 and dialyzing fluid flows through dialyzing fluid chamber 4 of the dialyzer. Balancing device 35 ensures that only as much dialyzing fluid can flow via the dialyzing fluid supply line as dialyzing fluid can flow away via the dialyzing fluid discharge line. By means of ultrafiltration pump 17, a preset quantity of fluid (ultrafiltrate) can be withdrawn from the patient at a preset ultrafiltration rate. Ultrafiltration pump 17 is therefore a part of a device for withdrawing fluid from the blood flowing in extracorporeal circuit 9 through membrane 2 of dialyzer 1, which is referred to as ultrafiltration device 18.

Instead of the arrangement shown in FIG. 2, other balancing devices are also commonly used. The decisive factor is that the supply of fluid to dialyzer 1 or the blood circuit and the discharge of fluid from the dialyzer are controlled.

In order to feed the fluid back to the patient, the hemodiafiltration apparatus has a substitution device 19, with which a substitution fluid (substituate) can be fed to the blood which is flowing through arterial branch 20 (pre-dilution) and/or venous branch 21 (post-dilution) of extracorporeal blood circuit 9. Substitution device 19 comprises a device 37 for making available substituate, from which device a first substituate line 36, in which a first substituate pump 22 is incorporated, leads to the section of blood supply line 5 between blood pump 6 and blood chamber 3. A second substituate line 23, in which a second substituate pump 24 is incorporated, leads from device 37 for making available substituate to drip chamber 8. If the hemodiafiltration apparatus is to be operated only with post-dilution or pre-dilution, the one or the other substituate pump together with the respective substituate line can be dispensed with.

Moreover, the hemodiafiltration apparatus comprises a central control and computing unit 25, which is connected via control lines 26 to 30 to blood pump 6, dialyzing fluid pump 14, ultrafiltration pump 17 and first and second substitute pump 22, 24.

The device according to the present invention for monitoring the dialyzer is described below as a component of the blood treatment apparatus, since the blood treatment apparatus already has the necessary hardware. The device according to the present invention, however, can in principle also be a separate unit.

The monitoring device has means for measuring oscillating pressure signals and means for analyzing the pressure signals, which means comprise a computing and evaluation unit 32 which can also be a component of central control and computing unit 25, as well as a pressure sensor 33 arranged downstream of blood chamber 3 on blood discharge line 7 and a pressure sensor 34 arranged downstream of dialyzing fluid chamber 4 of dialyzer 1 upstream of dialyzing fluid pump 14 on dialyzing fluid discharge line 13. Pressure sensors 33 and 34 are connected via data lines 38, 39 to computing and evaluation unit 32, which exchanges the necessary data via a data line 40 with central control and computing unit 25. Central control and computing unit 25 can intervene in the machine control when computing and evaluation unit 32 has detected a malfunction. The function of the monitoring device is described in detail below.

Computing and evaluation unit 32 has a Fourier analysis device 32A, which analyses either the output signal of pressure sensor 33 arranged in blood circuit 9 or that of pressure sensor 34 in dialyzing fluid circuit 10.

Blood pump 6 generates oscillating pressure pulses, which are propagated on the one hand via blood supply line 5 in the longitudinal direction of the fibers of membrane 2 of dialyzer 1 and blood discharge line 7 and are measured by pressure sensor 33, and on the other hand spread in the lateral direction to the blood flow in the dialyzer and are propagated via dialyzing fluid discharge line 13 and measured by pressure sensor 34.

Fourier analysis device 32A breaks down the oscillating pressure signals of pressure sensor 34 or of pressure sensor 33 by means of a Fourier analysis into the fundamental oscillation and several harmonics, for example the first and second harmonics.

In the first place, it is assumed that the hemodiafiltration apparatus is operated with a post-dilution, substitute pump 24 running and substitute pump 22 standing still. Control and computing unit 25 sets the delivery rate of substitute pump 24 in such a way that a preset quantity of substitute is fed to the blood in the blood circuit at a preset substitute rate, for example 20 l of substitute during the whole blood treatment. Ultrafiltrate pump 17 is operated by control and computing unit 25 at a delivery rate such that an ultrafiltration rate is set that corresponds to the level of the substitute rate, for example 16 l per treatment, i.e. the quantity of ultrafiltrate that is withdrawn from the dialyzing fluid system by pump 17 is compensated for by the same quantity of substitute which is fed to the blood circuit by pump 24. In total, 4 l of fluid, for example, is withdrawn from the patient during the treatment.

The pressure pulses in blood return line 7 are measured by venous pressure sensor 33 and the venous pressure signal is broken down by Fourier analysis device 32A of computing and evaluation unit 32 into the fundamental oscillation and the first and second harmonic. Computing and evaluation unit 32 calculates the amplitudes of the fundamental oscillation and of the first and second harmonics and in each case calculates the square of the amplitude ($U^2_{out}(\omega)$) from the amplitude of the fundamental oscillation and the first and second harmonics.

Substitute pump 24 is then stopped briefly, so that no substitute is fed to the blood circuit. It is however also possible either briefly to increase or reduce the delivery quantity of the substitute pump. While substitute pump 24 is stopped or the delivery quantity of the substitute pump is increased or reduced, ultrafiltration pump 17 is operated in such a way that the ultrafiltration rate is increased or reduced by the same amount as the substitute rate has increased or reduced. Evaluation and computing unit 32 breaks down the pressure signal of pressure sensor 33, with substitute pump 24 stationary, back into the fundamental oscillation and the first and second harmonic.

FIG. 3 shows the square of the amplitude $U_{out}^2$ of the fundamental oscillation and the first and second higher harmonics of the pressure signal of pressure sensor 33 as a function of the treatment time, substitute pump 24 being stopped briefly in preset time segments during the whole treatment. At the time when the substitute pump is stopped, the amplitudes of the fundamental oscillation and the harmonics of the pressure signal increase. This can clearly be seen in FIG. 3. Evaluation and computing unit 32 determines, by taking the difference before and after the change in the substitute and ultrafiltration rate, the level of the amplitude change and calculates the square of amplitude change $\Delta U_{out}^2$.

Computing and evaluation unit 32 calculates, according to equation (5), the change in the flow resistance $(R+\Delta R)/R$ from the square of the amplitude $\Delta U_{out}^2$ and the change in the square of the amplitude $\Delta U_{out}^2$.

Computing and evaluation unit 32 has a comparison unit 32B, which compares the calculated value for the change in the flow resistance $(R+\Delta R)/R$ with a preset threshold value. If the change in the flow resistance exceeds the threshold value, computing and evaluation unit 32 triggers control and computing device 25 of the dialysis apparatus, which can emit an acoustic and/or optical alarm or intervene in the machine control in order to prevent clogging of membrane 2 of dialyzer 1. Possible countermeasures are, for example, a reduction in the ultrafiltration rate, as a result of which the thickening of the blood is counteracted.

The table from FIG. 5 shows calculated quantities $U_{out}^2$ and $\Delta U_{out}^2$ as well as the change in the flow resistance $(R+\Delta R)/R$ at the start of the blood treatment in the middle of the blood treatment and at the end of the blood treatment for the fundamental oscillation as well as the first and second harmonics in the case of post-dilution.

The spectrally broken down contributions of the venous pressure signal during the blood treatment are a direct measure of the flow resistance of the dialyzer along the dialyzer fibers. With increasing flow resistance, the risk of fibers blocking up and hemolysis during the treatment increases. The flow resistance along the dialyzer fibers often increases sharply without being noticed during the treatment especially in the case of hemodiafiltration with post-dilution, so that the dialyzer can start to clot and the dialyzer inlet pressure can reach critical values. The method according to the present invention allows the increase in the flow resistance to be assessed during the hemodiafiltration treatment, so that countermeasures can be taken in order to keep the flow resistance constant or to reduce it.

It is assumed in the following that the hemodiafiltration apparatus is operated with pre-dilution, substitute pump 24 standing still and substitute pump 22 running, so that substitute is fed to blood circuit 9 upstream of dialyzer 1. The computing and evaluation unit continues to analyze the pressure signal of pressure sensor 33.

FIG. 4 shows the squares of the amplitude $U_{out}^2$ of the fundamental oscillation and of the first and second higher harmonics as a function of the treatment time in the case of hemodiafiltration with pre-dilution. It can be seen that the amplitude of the pressure signal of the fundamental oscillation and of the first and second harmonic increases when substitute pump 22 is stopped briefly. However, the effects are not as marked as in the case of post-dilution, since the blood flowing into blood chamber 3 of dialyzer 1 already has a lower viscosity, so that subsequent thickening can no longer have such a great influence on the viscosity of the flowing blood.

The table from FIG. 6 shows calculated quantities $\Delta U_{out}^2$ and $U_{out}^2$ as well as the change in the flow resistance $(R+\Delta R)/R$ at the start of the hemodiafiltration with pre-dilution, in the middle of the treatment and at the end of the treatment for the fundamental oscillation as well as the first and second higher harmonics.

The invention claimed is:

1. A device for monitoring a blood treatment unit for an extracorporeal blood treatment apparatus comprising:
   a blood treatment unit divided by a semipermeable membrane into a blood chamber and a dialysing fluid chamber;
   an extracorporeal blood circuit with an arterial branch that leads to the blood chamber, and a venous branch that leads away from the blood chamber, and a dialysing fluid system in which the dialysing fluid chamber is disposed;
   an ultrafiltration device for withdrawing ultrafiltrate at a preset ultrafiltration rate from the blood flowing in the extracorporeal blood circuit via the semipermeable membrane of the blood treatment unit; and
   a device for supplying substituate at a preset substituate rate upstream or downstream of the blood treatment unit to the blood flowing in the extracorporeal blood circuit;
   at least one device configured for measuring oscillating pressure signals in the extracorporeal blood circuit or in the dialysing fluid system, wherein the at least one device configured for measuring the oscillating pressure signals is configured such that, in the extracorporeal blood circuit or in the dialysing fluid system, an oscillating pressure signal is measured at a first time when at least one of the following occurs: substituate is provided at a preset first substituate rate upstream or downstream of the blood treatment unit to the extracorporeal blood circuit, or ultrafiltrate is withdrawn at a preset first ultrafiltration rate via the semipermeable membrane of the blood treatment unit, and an oscillating pressure signal is measured at a second time when at least one of the following occurs: substituate is fed at a preset second substituate rate to the extracorporeal blood circuit, or ultrafiltrate is withdrawn at a preset second ultrafiltration rate via the membrane of the blood treatment unit, wherein the preset second substituate rate differs from the preset first substituate rate, and the preset second ultrafiltration rate differs from the preset first ultrafiltration rate, and
   a unit configured for analyzing the pressure signals measured in the extracorporeal blood circuit or in the dialysing fluid system, wherein the unit configured for analyzing is configured such that, on a basis of the measured oscillating pressure signals before and after a change in at least one of the substituate rate and the ultrafiltration rate a quantity correlating with a change in flow resistance of the blood treatment unit is calculated.

2. The device according to claim 1, wherein the at least one device configured for measuring the oscillating pressure signals is further configured such that, at the first time when the substituate is fed at the preset first substituate rate, a preset quantity of ultrafiltrate is withdrawn at the preset first ultrafiltration rate from the extracorporeal blood circuit.

3. The device according to claim 2, wherein the ultrafiltration rate is increased or reduced by a same amount as the substituate rate.

4. The device according to claim 1, wherein the unit configured for analyzing the oscillating pressure signals is configured such that the quantity correlating with the change in the flow resistance is compared with a preset threshold value, and it is concluded that there is a critical state if the quantity correlating with the change in the flow resistance exceeds the preset threshold value.

5. The device according to claim 1, wherein the unit configured for analyzing the oscillating pressure signals is configured such that a frequency spectrum of the oscillating pressure signal measured before the change in the substituate rate and of the oscillating pressure signal measured after the change in the substituate rate is analyzed, and at least one of a change in an amplitude of the fundamental oscillation, and a change in an amplitude of at least one harmonic of the oscillating pressure signal before and after the change in the substituate rate is determined, and the change in the flow resistance is calculated on a basis of at least one of the change in the amplitude of the fundamental oscillation, and the change in the amplitude of the at least one harmonic of the oscillating pressure signal.

6. The device according to claim 5, wherein the unit configured for analyzing the oscillating pressure signals is configured such that at least one of a square of the amplitude $U^2(\omega)$ of the fundamental oscillation, and the amplitude of the at least one harmonic of the measured oscillating pressure signal is calculated before the change in the substituate rate and at least one of a square of the change $\Delta U^2(\omega)$ in the amplitude of the fundamental oscillation, and the amplitude of the at least one harmonic is calculated after the change in the substituate rate, and the change in the flow resistance R is calculated according to the following equation:

$$\frac{R+\Delta R}{R} \approx \sqrt{\frac{U_{out}^2(\omega)}{U_{out}^2(\omega) - \Delta U_{out}^2(\omega)}}.$$

7. The device according to claim 5, wherein the unit configured for analyzing the oscillating pressure signals comprises a device configured for performing a Fourier transform.

8. The device according to claim 1, wherein the blood treatment apparatus comprises a blood pump arranged in the arterial branch of the extracorporeal blood circuit which generates an oscillating pressure signal.

9. The device according to claim 8, wherein the at least one device configured for measuring the oscillating pressure signals comprises a pressure sensor that measures a pressure in the venous branch of the extracorporeal blood circuit.

10. The device according to claim 8, wherein the dialyzing fluid system comprises a dialyzing fluid supply line leading to the dialyzing fluid chamber of the blood treatment unit and a dialyzing fluid discharge line leading away from the dialysing fluid chamber, and the at least one device configured for measuring the oscillating pressure signals comprises a pressure sensor that measures a pressure in the dialysing fluid discharge line.

11. The device according to claim 8, wherein the blood pump is an occluding blood pump.

* * * * *

UNITED STATES PATENT AND TRADEMARK OFFICE
CERTIFICATE OF CORRECTION

PATENT NO.       : 8,574,183 B2
APPLICATION NO.  : 12/598250
DATED            : November 5, 2013
INVENTOR(S)      : Pascal Kopperschmidt Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 740 days.

Signed and Sealed this
Twenty-second Day of September, 2015

Michelle K. Lee
*Director of the United States Patent and Trademark Office*